(12) United States Patent
Allen et al.

(10) Patent No.: US 7,577,477 B2
(45) Date of Patent: Aug. 18, 2009

(54) PERIVASCULAR LEAK REPAIR SYSTEM

(75) Inventors: Jeffrey W. Allen, Santa Rosa, CA (US); David S. Brin, Topsfield, MA (US); Chris M. Coppin, Carlsbad, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 562 days.

(21) Appl. No.: 10/835,189

(22) Filed: Apr. 29, 2004

(65) Prior Publication Data

US 2004/0249413 A1 Dec. 9, 2004

Related U.S. Application Data

(60) Provisional application No. 60/467,054, filed on Apr. 30, 2003.

(51) Int. Cl.
*A61N 1/30* (2006.01)
*A61M 31/00* (2006.01)
*A61B 17/08* (2006.01)
*A61F 2/24* (2006.01)

(52) U.S. Cl. ............................ 604/21; 604/67; 606/213; 623/2.1

(58) Field of Classification Search ......... 606/213–215, 606/169–171; 604/537, 19–22, 49, 4.01, 604/5.01, 65–67, 214; 600/202; 623/2.1–2.19
See application file for complete search history.

(56) References Cited

U.S. PATENT DOCUMENTS

| | | | | |
|---|---|---|---|---|
| 5,603,704 A | * | 2/1997 | Brin et al. ................... 604/532 |
| 5,797,960 A | * | 8/1998 | Stevens et al. ............... 606/213 |
| 6,010,531 A | * | 1/2000 | Donlon et al. ................ 623/2.1 |
| 6,287,271 B1 | * | 9/2001 | Dubrul et al. ................. 604/22 |
| 6,302,898 B1 | * | 10/2001 | Edwards et al. ............. 606/214 |
| 6,425,866 B1 | * | 7/2002 | Brucher et al. .............. 600/438 |
| 6,475,466 B1 | * | 11/2002 | Ricci et al. .................. 424/9.45 |
| 6,685,727 B2 | * | 2/2004 | Fisher et al. ................. 606/213 |
| 6,743,248 B2 | * | 6/2004 | Edwards et al. ............. 606/214 |
| 6,770,070 B1 | * | 8/2004 | Balbierz ....................... 606/41 |
| 6,818,006 B2 | * | 11/2004 | Douk et al. .................. 606/200 |
| 6,866,677 B2 | * | 3/2005 | Douk et al. .................. 606/200 |
| 6,959,214 B2 | * | 10/2005 | Pape et al. ..................... 607/17 |
| 6,983,179 B2 | * | 1/2006 | Ben-Haim ................... 600/374 |
| 2002/0173770 A1 | * | 11/2002 | Flory et al. .................. 604/537 |

* cited by examiner

*Primary Examiner*—Leslie R Deak
*Assistant Examiner*—Phil Wiest

(57) ABSTRACT

The perivascular leak repair system, and method of using the same, of the present invention provides a sealant reservoir with a repair catheter operably attached; a flow control device disposed between the sealant reservoir and the repair catheter, and the flow control device responsive to a flow control signal; a heart phase detector generating a diastole phase signal; an injection switch generating a injection signal; and a flow controller responsive to the diastole phase signal and the injection signal, and generating the flow control signal. A method of sealing a perivascular leak comprises identifying the perivascular leak; inserting a repair catheter to the perivascular leak; injecting sealant at the perivascular leak; and removing the repair catheter. The sealant can be injected when the heart is in diastole to sweep the sealant into the perivascular leak.

10 Claims, 6 Drawing Sheets

PERIVASCULAR LEAK REPAIR SYSTEM

RELATED APPLICATION

This application claims priority to U.S. Provisional Application No. 60/467,054, "Perivascular Leak Repair System" to Jeffrey W. Allen, et al., filed Apr. 30, 2003, the entirety of which is incorporated by reference.

TECHNICAL FIELD

The technical field of this disclosure is medical devices, particularly, perivascular leak repair systems and method of using the same.

BACKGROUND OF THE INVENTION

Heart valves, such as the aortic valve, are sometimes damaged by disease or by aging, which can cause problems with the proper function of the valve. Heart valve problems generally take one of two forms: stenosis, in which a valve does not open completely or the opening is too small, resulting in restricted blood flow; or insufficiency, in which blood leaks backward across the valve that should be closed. Valve replacement may be required in severe cases to restore cardiac function.

Valve replacement can be performed through open-heart surgery, open chest surgery, or percutaneously. The native valve is removed and replaced with a prosthetic valve, or a prosthetic valve is placed over the native valve. The open chest and percutaneous procedures avoid opening the heart and cardiopulmonary bypass. Regardless of the procedure used, perivascular leakage can occur around the prosthetic valve and cannot be detected until the heart is closed and beating.

FIG. 1 shows a prosthetic aortic valve implanted in the aorta. Perivascular leakage, i.e., back flow from the ascending aorta 20 to the left ventricle 22 during diastole, will occur if the prosthetic aortic valve 24 is not sealed in the aorta, creating a perivascular leak 26. Some perivascular leakage may heal shut over time, but the healing is uncertain and the leakage reduces valve function until the healing is complete. Currently, repair of perivascular leakage requires an open-heart surgery to repair the leak with additional sutures. Repair may also require replacement of the prosthetic valve if the prosthetic valve size is incorrect. Open-heart surgery involves risk, expense, and an extended recovery time. Open-heart surgery also requires cardiopulmonary bypass with risk of thrombosis, stroke, and myocardial infarction.

It would be desirable to have a perivascular leak repair system that would overcome the above disadvantages.

SUMMARY OF THE INVENTION

One aspect of the present invention provides a perivascular leak repair system that provides immediate perivascular leak repair.

Another aspect of the present invention provides a perivascular leak repair system that avoids open-heart surgery for perivascular leak repair.

Another aspect of the present invention provides a perivascular leak repair system that uses leakage flow to carry sealant into the perivascular leak.

Another aspect of the present invention provides a perivascular leak repair system that avoids injecting unnecessary sealant in the circulatory system.

The foregoing and other features and advantages of the invention will become further apparent from the following detailed description of the presently preferred embodiments, read in conjunction with the accompanying drawings. The detailed description and drawings are merely illustrative of the invention, rather than limiting the scope of the invention being defined by the appended claims and equivalents thereof.

DETAILED DESCRIPTION OF THE PRESENTLY PREFERRED EMBODIMENT

Figure 1:
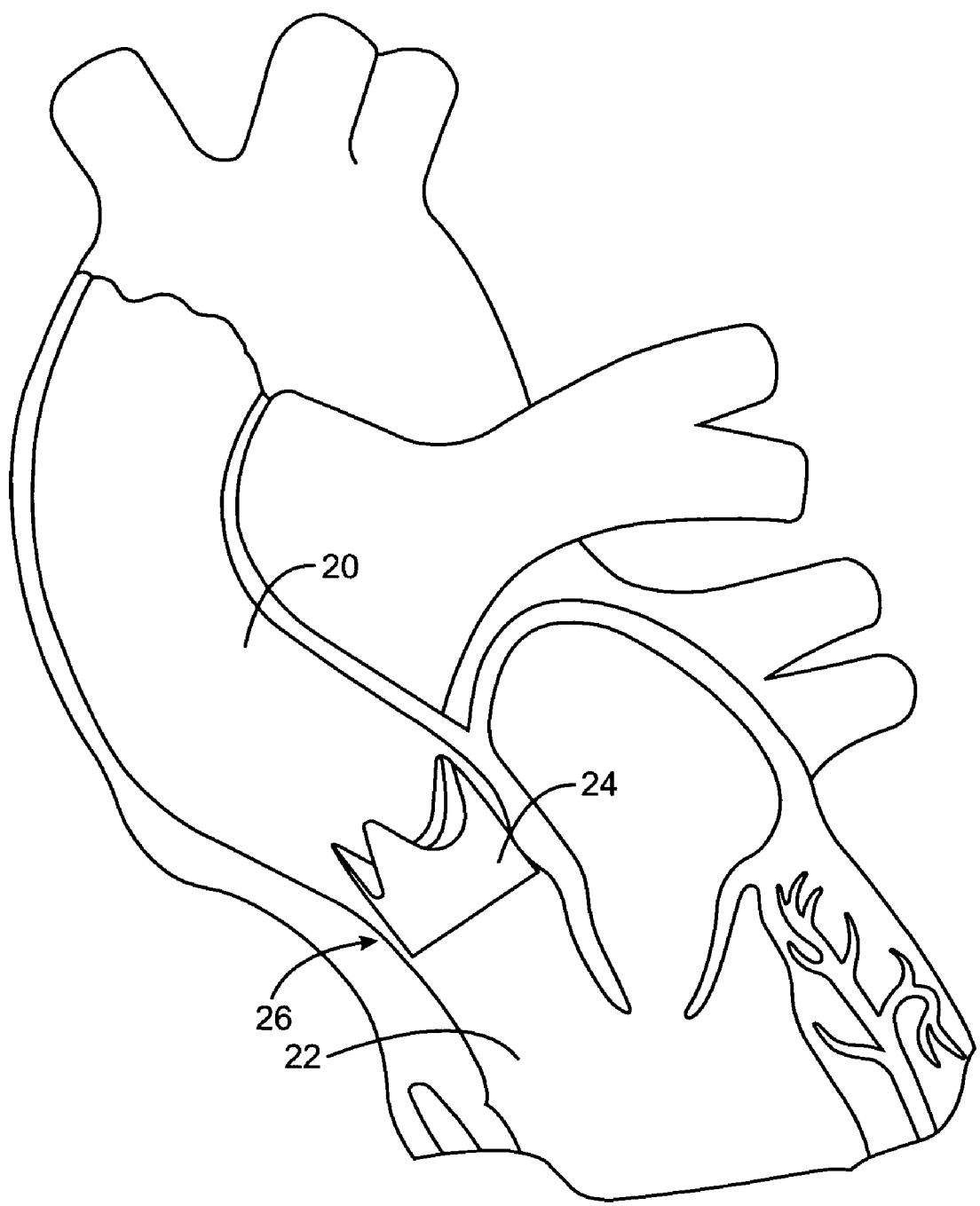
FIG. 1 shows a prosthetic aortic valve implanted in the aorta.
Figure 2:
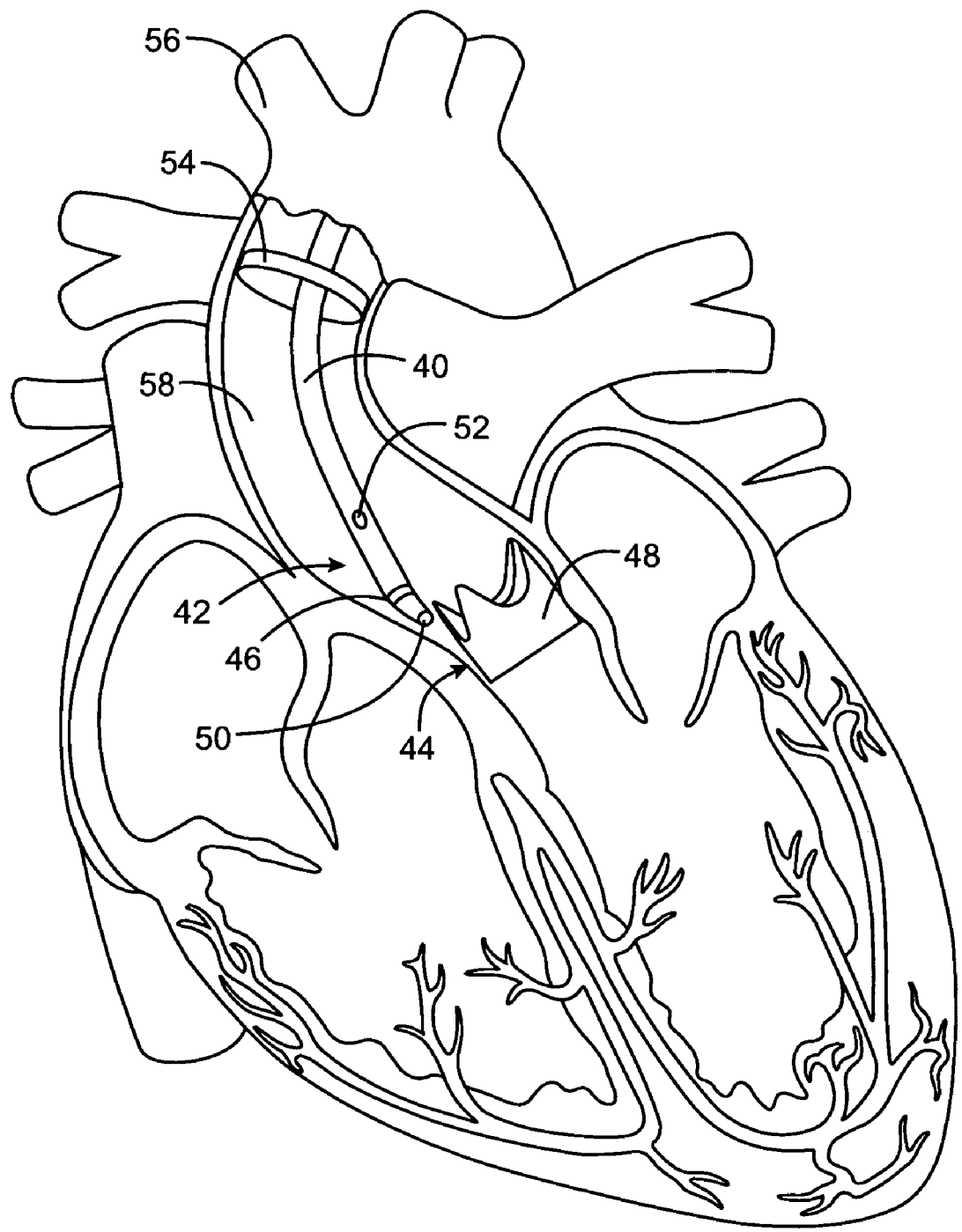
FIG. 2 shows a perivascular leak repair system inserted percutaneously and made in accordance with the present invention.

FIG. 2 shows a perivascular leak repair system inserted percutaneously. A repair catheter is advanced percutaneously to the perivascular leak and sealant injected at the perivascular leak. The sealant injection can be coordinated with the heartbeat to sweep the sealant into the perivascular leak.

In the example shown, the repair catheter 40 can be inserted inguinally into the femoral artery and advanced until the distal tip 42 is near the perivascular leak 44 at the prosthetic aortic valve 48. The location of the perivascular leak 44 can be determined using echocardiography before inserting the repair catheter 40. The location of the distal tip 42 relative to the perivascular leak 44 can be determined by an imaging or navigation system. In one embodiment, the distal tip 42 can have a radiopaque marker 46 and fluoroscopy can be used to locate the distal tip 42. In another embodiment, a non-fluoroscopic navigation system, such as the Localisa® intracardiac navigation system from Medtronic, Inc., of Minneapolis, Minn., can be used to locate the distal tip 42. The Localisa® intracardiac navigation system uses three skin electrode pairs, positioned in x, y, z directions around the heart to track catheters. In yet another embodiment, fluoroscopy can be used in conjunction with a non-fluoroscopic navigation system to locate the distal tip 42.

The repair catheter 40 can be any catheter that can locate a distal tip 42 near the perivascular leak 44 and includes a lumen 50 to inject a sealant. In one embodiment, the repair catheter 40 can be steerable, such as the MyoCath™ catheter from Bioheart, Inc., MyoStar catheter from Johnson & Johnson, Inc., or the Stiletto catheter from Boston Scientific, Inc. In another embodiment, the distal tip 42 can have retractable needle or corkscrew elements to connect the distal tip 42 with the cardiac tissue at the perivascular leak 44.

When the distal tip 42 is at or near the perivascular leak 44, a sealant can be injected through a lumen 50 in the repair catheter 40 to seal the perivascular leak 44. The sealant can be any non-toxic sealant that can flow into or cover over the perivascular leak 44. The sealant can flow into and adhere to the walls of the perivascular leak 44. The sealant can degrade with time with tissue ingrowth maintaining the seal.

The sealant can use the body's own clotting and repair mechanisms to stop the perivascular leak. In one embodiment, the sealant can be fibrin glue. Fibrin glues are typically made by contacting a solution or suspension of the blood protein fibrinogen with an enzyme or other reagent which can crosslink it. Typically, the enzyme thrombin is used, which cleaves the fibrinogen molecule, forming fibrin monomer which then spontaneously polymerizes. This is a natural reaction involved in the formation of blood clots. Fibrinogen can be obtained from the patient or from pooled homologous human blood. The blood protein fibrinogen and enzyme thrombin can be injected through separate lumens in the repair catheter so that the two components meet and mix at the perivascular leak. In another embodiment, the sealant can be collagen paste. Collagen paste is typically collagenous material ground to a fine powder and mixed with water or aqueous saline solution until injectable. The collagen paste is thrombogenic, so that it will form clots and recruit fibrin in the perivascular leak.

Other sealants which can be used to seal the perivascular leak include, but are not limited to, activated platelet gel, hydrogels, N-butyl cyanoacrylate, isobutyl-2 cyanoacrylate, alykyl cyanoacrylate, silicone rubber, Ethibloc amino acid gel, autologous material such as fat dura, EVAL ethylene vinyl alcohol copolymer, EMBOLYX ethylene vinyl alcohol copolymer, poly-vinyl alcohol, alginates such as polysachrides, posphoryl choline-hydrogel, activated microparticles, combinations thereof, and the like.

The repair catheter 40 can also have a pressure sensor 52 for sensing pressure in the ascending aorta 58. The pressure sensor 52 can transmit a pressure signal to the heart phase detector, which can use the pressure signal to determine when the heart is in diastole. Sealant injected during diastole will follow the backflow from the ascending aorta 58 into the perivascular leak 44 to provide a superior seal without releasing substantial sealant into the circulatory system. In one embodiment, the repair catheter 40 can include a pressure lumen exiting near the distal tip 42 to transmit the pressure in the ascending aorta 58 to a pressure sensor mounted external to the patient or mounted proximally the distal tip 42 within the repair catheter 40 itself. In yet another embodiment, the pressure sensor can be omitted and an electrocardiogram (ECG) used to determine diastole. In yet another embodiment, the repair catheter 40 can include a Doppler echo probe for detecting flow and determining diastole. The Doppler echo probe can also be used for imaging the perivascular leak, the prosthetic valve, and the surrounding structure. The Doppler echo probe can also be used to detect emboli.

A filter 54 can be disposed on the repair catheter 40 across the ascending aorta 58 before the brachiocephalic artery to catch and retain sealant or other emboli discharged during the perivascular leak repair procedure. In another embodiment, a separate filtering device, such as the Scion Cardio-Vascular SCI-PRO® guide wire based retrieval device from Scion Cardio-Vascular, Inc., of Miami, Fla., can be inserted in parallel with the repair catheter 40 to remove embolic material during the perivascular leak repair.

Figure 3:
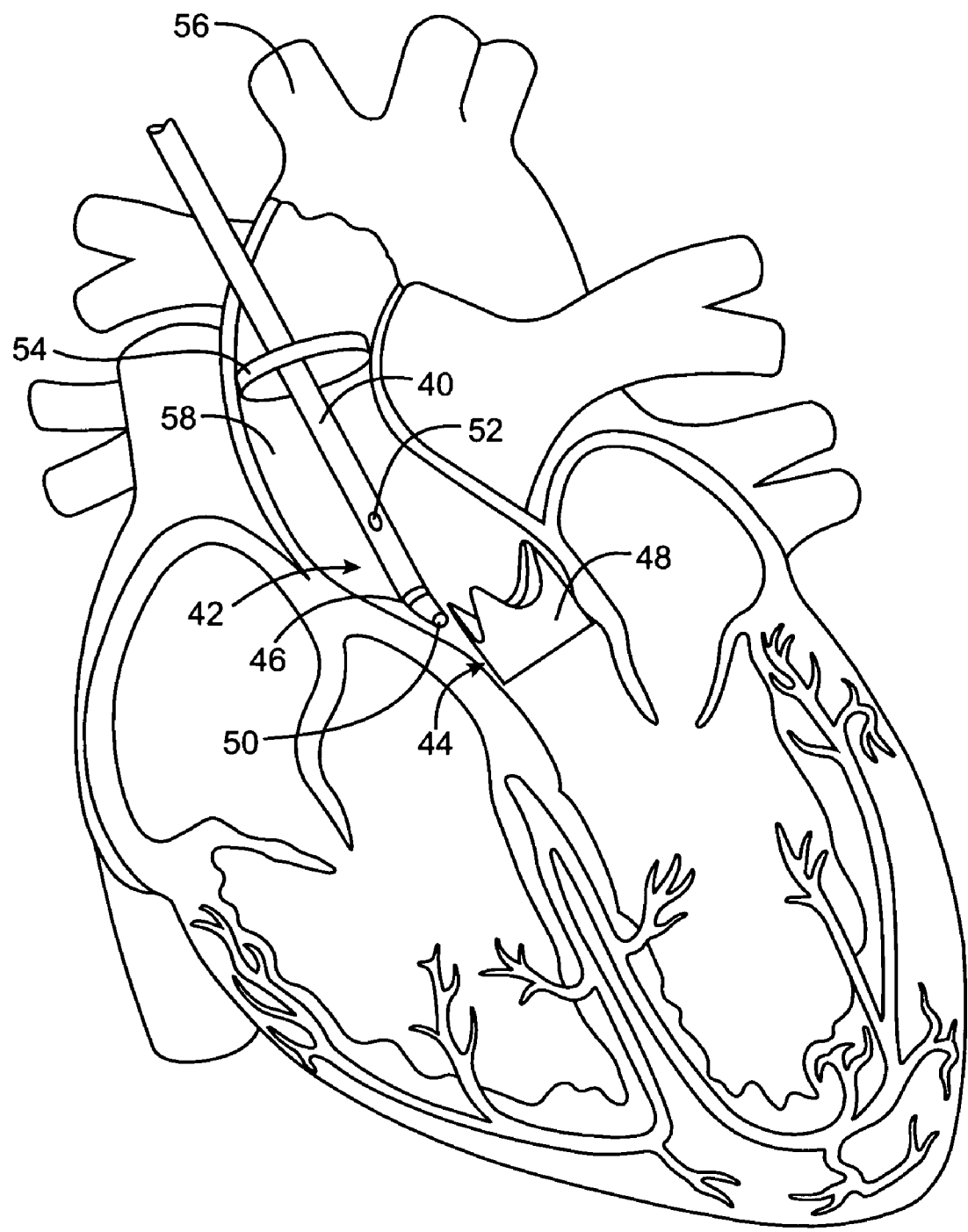
FIG. 3 shows a perivascular leak repair system inserted through the aortic wall and made in accordance with the present invention.

FIG. 3, in which like elements share like reference numbers with FIG. 2, shows a perivascular leak repair system inserted through the aortic wall. Accessing the perivascular leak 44 through the aortic wall avoids opening the heart itself and is possible when the chest is open. This approach is particularly advantageous if a perivascular leak is discovered after open chest valve replacement surgery, but before the chest is closed. A repair catheter 40 is placed through the aortic wall and sealant injected at the perivascular leak 44 from the lumen 50. The sealant injection can be coordinated with the heartbeat to sweep the sealant into the perivascular leak.

Figure 4A:
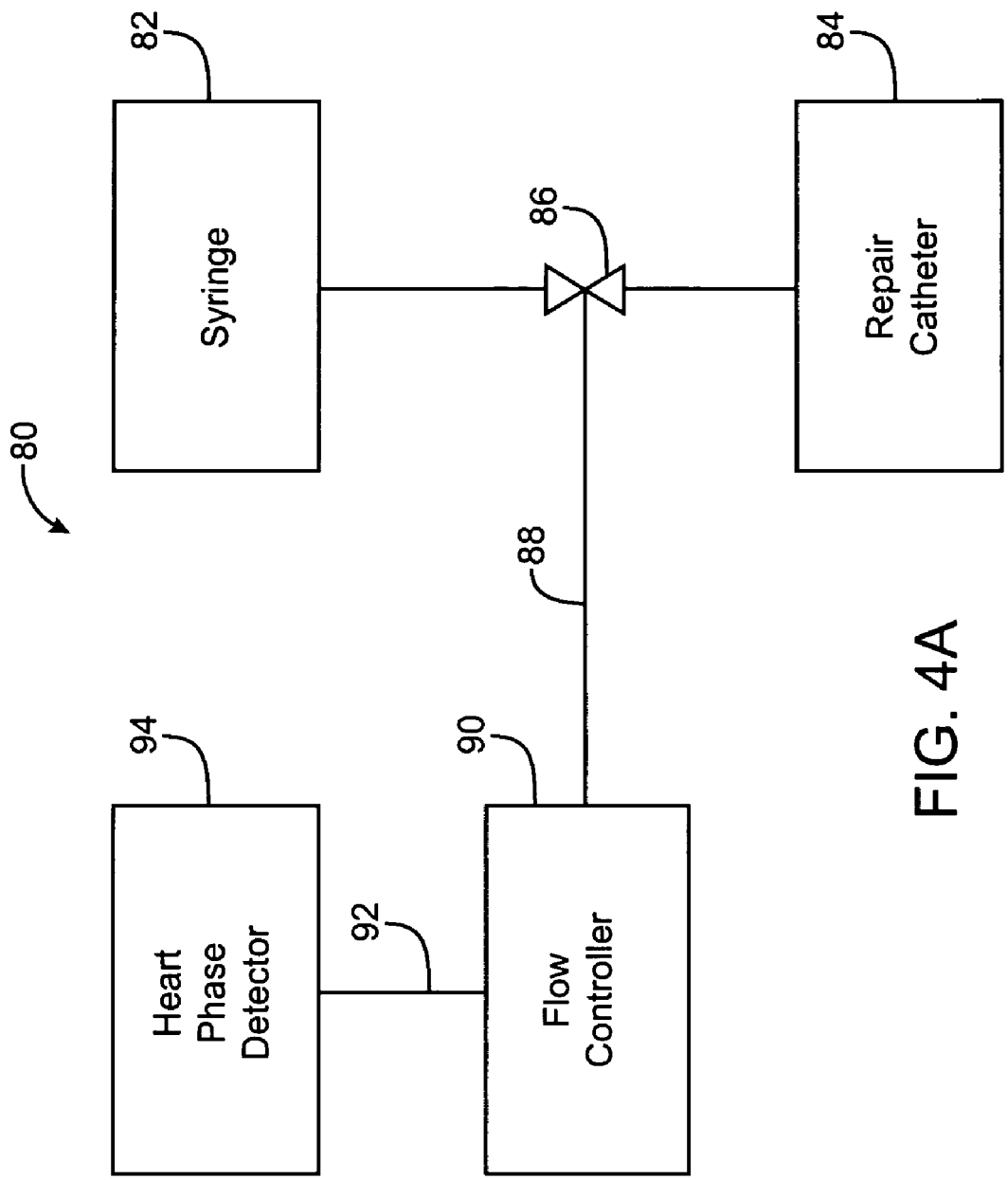
FIGS. 4A & 4B show detailed and general block diagrams, respectively, of a perivascular leak repair system made in accordance with the present invention.
Figure 4B:
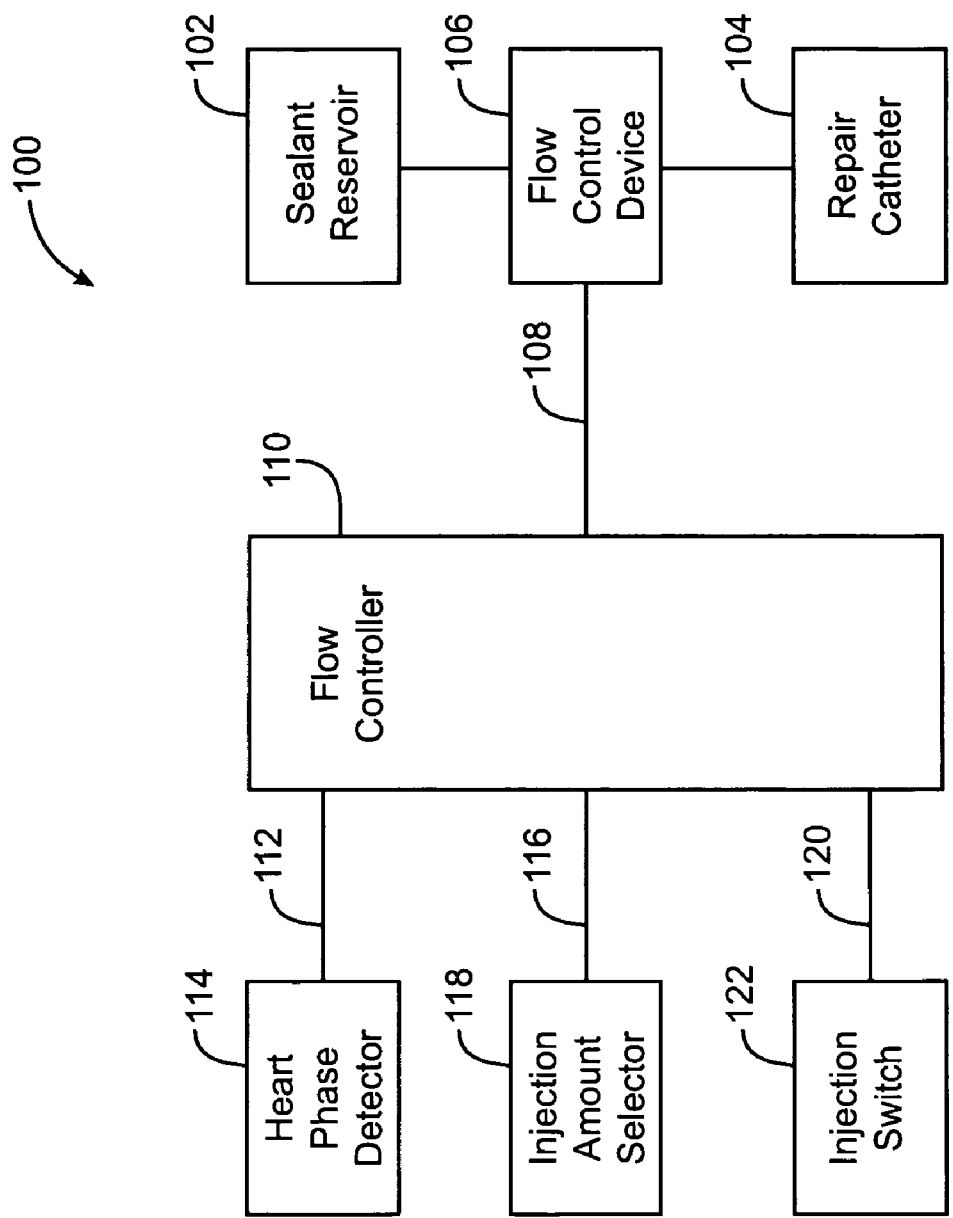

FIGS. 4A & 4B show detailed and general block diagrams, respectively, of a perivascular leak repair system. The control system coordinates sealant injection with the heartbeat to sweep the sealant into the perivascular leak.

FIG. 4A shows one embodiment of perivascular leak repair system. The perivascular leak repair system 80 comprises a syringe 82 providing sealant to a repair catheter 84 through a flow control valve 86. The flow control valve 86 is responsive to a flow control signal 88 from a flow controller 90 to stop or allow sealant flow from the syringe 82 to the repair catheter 84. The flow controller 90 is responsive to a diastole phase signal 92 from the heart phase detector 94.

In use, the repair catheter 84 is advanced so that the distal tip is near the perivascular leak. The syringe 82 and flow control valve 86 remain outside the patient. The heart phase detector 94 monitors heartbeat using pressure at the distal tip of the repair catheter 84 or an electrocardiogram (ECG). When the heart phase detector 94 detects the heart is in diastole, the heart phase detector 94 sends a diastole phase signal 92 to the flow controller 90 indicating the same. The flow controller 90, in turn, sends a flow control signal 88 to the flow control valve 86 directing the flow control valve 86 to permit flow. If the surgeon is applying pressure to the syringe 82, sealant will flow through the flow control valve 86 and the repair catheter 84 to enter the perivascular leak with the backflow through the perivascular leak. During systole, the flow control valve 86 is closed and no flow is permitted through the repair catheter 84. Applying sealant during diastole, and not during systole, gets the sealant into the perivascular leak where required and avoids excess sealant being carried into the circulatory system.

FIG. 4B shows another embodiment of perivascular leak repair system. The perivascular leak repair system 100 comprises a sealant reservoir 102 providing sealant to a repair catheter 104 through a flow control device 106. The flow control device 106 is responsive to a flow control signal 108 from a flow controller 110 to stop or allow sealant flow from the sealant reservoir 102 to the repair catheter 104. The flow controller 110 is responsive to a diastole phase signal 112 from the heart phase detector 114 and an injection signal 120 from the injection switch 122. The flow controller 110 can also be responsive to an injection amount signal 116 from the injection amount selector 118.

The sealant reservoir 102 and flow control device 106 are selected to provide sealant flow to the repair catheter 104. In one embodiment, the sealant reservoir 102 can be pressurized and the flow control device 106 can be a valve. In another embodiment, the flow control device 106 can be a pump. Separate sealant reservoirs and flow paths can be provided for multi-part sealants that activate on mixing.

In use, the repair catheter 104 is advanced so that the distal tip is near the perivascular leak. The sealant reservoir 102 and flow control device 106 remain outside the patient. The heart phase detector 114 monitors heartbeat using pressure at the distal tip of the repair catheter 104, an electrocardiogram (ECG), or a Doppler echo probe. When heart phase detector 114 detects the heart is in diastole, the heart phase detector 114 sends a diastole phase signal 112 to the flow controller 110 indicating the same. When the injection switch 122 is activated by the surgeon providing an injection signal 120 to the flow controller 110, and the heart phase detector 94 detects the heart is in diastole providing a diastole phase signal 92, the flow controller 110 sends a flow control signal 108 to the flow control device 106 directing the flow control device 106 to permit flow. Sealant will flow through the flow control device 106 and the repair catheter 104 to enter the perivascular leak with the backflow through the perivascular leak each time the heart is in diastole until the surgeon releases the injection switch 122. Flow is stopped each time the heart is in systole, even though the surgeon maintains the injection switch 122 in the inject position. The flow controller 110 can also be responsive to an injection amount signal 116 from the injection amount selector 118 to limit to a predetermined amount the amount of sealant injected each time the heart is in diastole or to limit the amount of sealant injected each time the surgeon pushes the injection switch 122.

Emboli detection can be provided to detect emboli that might occur from or during the procedure. In one embodiment, the emboli detector can be a Doppler echo probe disposed on the repair catheter 104. In another embodiment, the emboli detector can be external, such as transcranial Doppler (TCD) ultrasound or the like.

Figure 5:
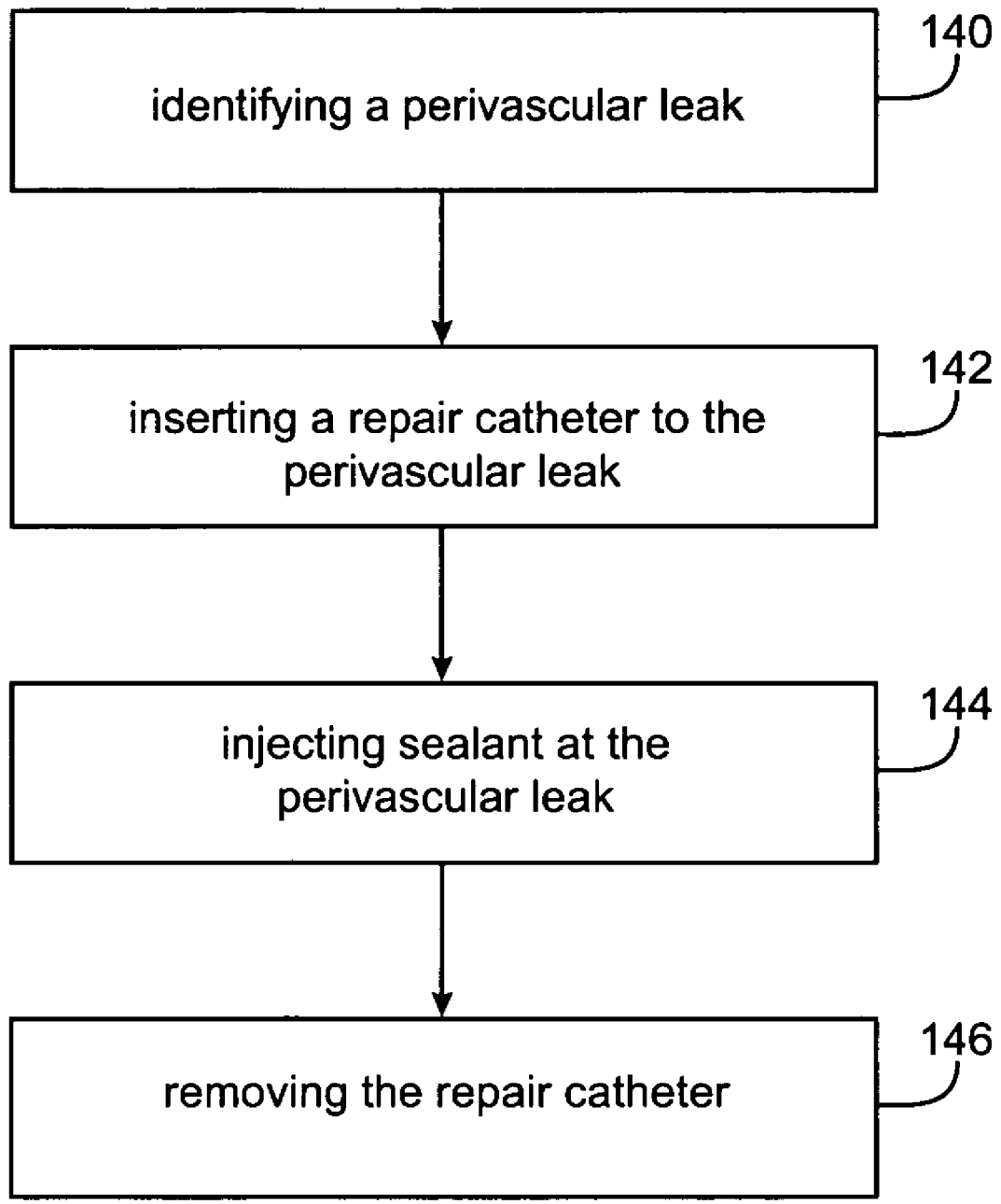
FIG. 5 shows a flow chart for a method of using a perivascular leak repair system made in accordance with the present invention.

FIG. 5 shows a flow chart for a method of using a perivascular leak repair system. A perivascular leak is identified at 140. A repair catheter is inserted to the perivascular leak 142 and sealant injected at the leak 144. The repair catheter is removed at 146. Typically, the sealant can be fibrin glue, collagen paste, activated platelet gel, or the like.

Identifying the perivascular leak 140 can comprise identifying the perivascular leak by echocardiography. While the repair catheter is inserted to the perivascular leak 142, the repair catheter can be located by an imaging or navigation system, such as fluoroscopy or a Localisa® non-fluoroscopic intracardiac navigation system from Medtronic, Inc. Injecting sealant at the perivascular leak 144 can comprise monitoring heart phase for diastole and injecting sealant at the perivascular leak during the diastole, and further comprise not injecting sealant during systole. The method can further comprise checking whether the perivascular leak is sealed and injecting sealant at the perivascular leak if the perivascular leak is not sealed. This can be repeated until the perivascular leak is sealed.

It is important to note that FIGS. 1-5 illustrate specific applications and embodiments of the present invention, and is not intended to limit the scope of the present disclosure or claims to that which is presented therein. For example, the perivascular leak repair system of the present invention can be used for other heart valves in addition to the aortic valve. Different arterial and venous approaches to the perivascular leak can also be used. Upon reading the specification and reviewing the drawings hereof, it will become immediately obvious to those skilled in the art that myriad other embodiments of the present invention are possible, and that such embodiments are contemplated and fall within the scope of the presently claimed invention.

While the embodiments of the invention disclosed herein are presently considered to be preferred, various changes and modifications can be made without departing from the spirit and scope of the invention. The scope of the invention is indicated in the appended claims, and all changes that come within the meaning and range of equivalents are intended to be embraced therein.

The invention claimed is:

1. A perivascular leak repair system for use with a heart comprising:
   a sealant reservoir;
   a repair catheter, the repair catheter being operably attached to the sealant reservoir;
   a flow control device, the flow control device being disposed between the sealant reservoir and the repair catheter, and being responsive to a flow control signal;
   a heart phase detector, the heart phase detector being configured to generate a diastole phase signal;
   an injection switch, the injection switch being configured to generate a injection signal; and
   a flow controller, the flow controller being responsive to the diastole phase signal and the injection signal, and being configured to generate the flow control signal;
   wherein the flow control device is configured to permit flow of sealant from the sealant reservoir during diastole and to prevent the flow of the sealant from the sealant reservoir during systole.

2. The system of claim 1 further comprising an injection amount selector, the injection amount selector being configured to generate an injection amount signal, wherein the flow controller is responsive to the injection amount signal.

3. The system of claim 1 wherein the heart phase detector is configured to monitor heartbeat using input from a device selected from the group consisting of a pressure sensor disposed on the repair catheter, a Doppler echo probe disposed on the repair catheter, and an electrocardiogram.

4. The system of claim 1 wherein the sealant reservoir is pressurized and the flow control device is a valve.

5. The system of claim 1 wherein the flow control device is a pump.

6. The system of claim 1 wherein the repair catheter is steerable.

7. The system of claim 1 further comprising a filter disposed on the repair catheter 40.

8. The system of claim 1 further comprising a pressure sensor disposed on the repair catheter.

9. The system of claim 1 further comprising a Doppler echo probe disposed on the repair catheter.

10. The system of claim 1 further comprising an emboli detector.

* * * * *

UNITED STATES PATENT AND TRADEMARK OFFICE
CERTIFICATE OF CORRECTION

PATENT NO. : 7,577,477 B2
APPLICATION NO. : 10/835189
DATED : August 18, 2009
INVENTOR(S) : Allen et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 829 days.

Signed and Sealed this

Seventh Day of September, 2010

David J. Kappos
*Director of the United States Patent and Trademark Office*